(12) United States Patent
Kathe et al.

(10) Patent No.: US 8,889,070 B2
(45) Date of Patent: Nov. 18, 2014

(54) METHOD AND APPARATUS FOR REMOVING CHLORIDE FROM SAMPLES CONTAINING VOLATILE ORGANIC CARBON

(75) Inventors: Ulrich Kathe, Leonberg (DE); Andrea Gross, Wiernzheim-Serres (DE); Anja Gerlinger, Stuttgart (DE)

(73) Assignee: Endress + Hauser Conducta Gesellschaft für- und Regeltechnik mbH + Co. KG, Gerlingen (DE)

( * ) Notice: Subject to any disclaimer, the term of this patent is extended or adjusted under 35 U.S.C. 154(b) by 511 days.

(21) Appl. No.: 12/923,628

(22) Filed: Sep. 30, 2010

(65) Prior Publication Data
US 2011/0083557 A1    Apr. 14, 2011

(30) Foreign Application Priority Data

Oct. 9, 2009   (DE) .......................... 10 2009 045 529

(51) Int. Cl.
*G01N 33/18* (2006.01)
*G01N 1/38* (2006.01)
*B01D 47/00* (2006.01)
*B01D 53/14* (2006.01)
*G01N 1/40* (2006.01)

(52) U.S. Cl.
CPC .......... *G01N 1/4044* (2013.01); *G01N 33/1826* (2013.01); *G01N 1/38* (2013.01)
USPC ......... 422/68.1; 422/82.05; 422/527; 96/413; 73/53.01; 73/61.48; 73/61.72; 73/863.21

(58) Field of Classification Search
None
See application file for complete search history.

(56) References Cited

U.S. PATENT DOCUMENTS

| 2,950,170 A | * | 8/1960 | Harnisch et al. .............. 423/488 |
| 4,203,964 A | | 5/1980 | Reinhardt |
| 4,977,094 A | * | 12/1990 | Goldstein et al. ............. 436/157 |

FOREIGN PATENT DOCUMENTS

DE            29 32 444 A1    2/1981

OTHER PUBLICATIONS

Norm DIN 38409-41 1980 12-00 Summarische Wirkungs—und Stoffkenngrossen.

* cited by examiner

*Primary Examiner* — Duane Smith
*Assistant Examiner* — Pankti Patel
(74) *Attorney, Agent, or Firm* — Bacon & Thomas, PLLC

(57) ABSTRACT

A method for removing chloride from samples containing volatile organic carbon, wherein a chloride containing sample is mixed with a difficultly volatile acid, wherein hydrochloric acid gas arises, which is present in dissolved form in a sample-acid mixture and then the hydrochloric acid gas is purged by a carrier gas from the sample-acid mixture, wherein the hydrochloric acid gas is removed from the carrier gas following the purging and the carrier gas is fed back to the sample-acid mixture. In order during the hydrochloric acid purging largely to suppress the driving out of easily volatile organic compounds, the sample-acid mixture has a temperature of approximately 3° C. to 30° C., wherein, following the purging from the sample-acid mixture, the hydrochloric acid gas is removed from the carrier gas by absorption with water.

17 Claims, 1 Drawing Sheet

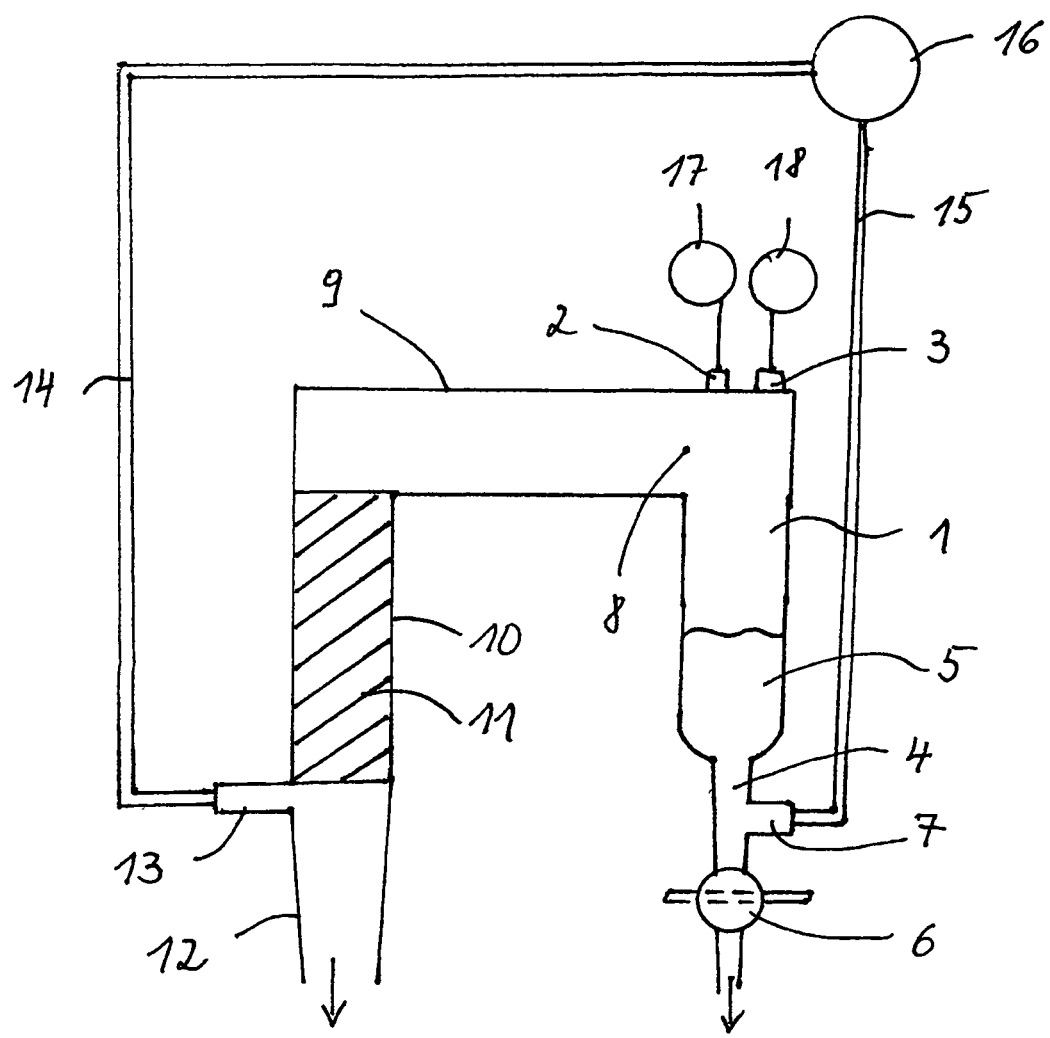

METHOD AND APPARATUS FOR REMOVING CHLORIDE FROM SAMPLES CONTAINING VOLATILE ORGANIC CARBON

TECHNICAL FIELD

The invention relates to a method for removing chloride from samples containing volatile organic carbon, wherein a chloride containing sample is mixed with a difficultly volatile acid, wherein hydrochloric acid gas arises, which is present in dissolved form in the sample-acid mixture and then the hydrochloric acid gas is purged from the sample-acid mixture using a carrier gas, wherein the hydrochloric acid gas is removed from the carrier gas following the purging and the carrier gas fed back to the sample-acid mixture. The invention relates also to an apparatus for performing the method.

BACKGROUND DISCUSSION

For establishing the cleanliness of flowing waters, or in wastewater- and clarification plants, the liquids in TOC (total organic carbon) samples, in which also volatile organic carbons (VOC volatile organic carbon) are contained, are examined for organic carbon content or for chemical oxygen demand (COD). The COD-value is an important parameter for classifying the degree of fouling of river water and in wastewater- and clarification plants. The fundamental principle of most methods for determining chemical oxygen demand involves treating a sample with a known excess of an oxidizing agent and then ascertaining consumption of oxidizing agent. The amount of consumed oxidizing agent is converted into the equivalent amount of oxygen.

Another method for digesting TOC-samples involves the application of UV-radiation.

Contained in the reaction mixture, however, are chloride ions, which disturb the ascertaining of the chemical oxygen demand, because they likewise consume oxidizing agent and so indicate either a too high chemical oxygen demand or mean that insufficient oxidizing agent is present for converting all TOC into carbon dioxide $CO_2$. For suppressing this effect, it is known to add to the reaction mixture mercury salts for masking the chloride ions in the liquid sample. Most often, mercury sulfate is applied. This salt has the greatest effectiveness, when it is present in a 10-times excess in comparison to the chloride content. The application of a so strong poison, as characterizes mercury sulfate in this concentration, however, burdens and endangers the operating personnel and the environment. The reaction mixture cannot be fed directly back into the water system, but, instead, must be treated and disposed of complicatedly and at high cost.

Known from DE 29 32 444 A1 is a method for separating disturbing components from a liquid, in the case of which a liquid sample is acidified with a difficultly volatile acid, wherein the chloride ions react with the acid to form hydrochloric acid gas. Then, the arising hydrogen chloride gas is purged from the liquid sample using a carrier gas. In such case, the vessel containing the liquid sample is heated. The sample-acid mixture is heated to a temperature between 30° C. and 60° C. The carrier gas is fed into the heated reactor containing the liquid sample and the acids and then brought through a removal system, where the hydrochloric acid gas deposits on the inner surface of the removal system, which is cooler than the reactor, and is absorbed by condensed water from the liquid sample. The carrier gas is fed via a pump system back to the sample-acid mixture in the reactor. By heating the sample-acid mixture, the vapor pressure of the VOC fractions in the sample is increased, so that the VOC is driven out of the sample with the carrier gas and is no longer available for the analysis.

SUMMARY OF THE INVENTION

An object of the invention is, thus, to provide a method and an apparatus for safely removing chloride ions from samples containing volatile organic carbon.

According to the invention, the object is achieved by the features that: the sample-acid mixture is unheated; and the hydrochloric acid gas, following the purging from the sample-acid mixture, is removed by absorption in water from the carrier gas. Because the partial pressure of the VOC is kept low due to the used reaction temperature of the sample-acid mixture, the VOC remains largely in the sample and is only driven out remains in a minimum amount. The sample, thus, available to the analytical procedure, while the hydrochloric acid gas dissolved in the sample-acid mixture is reliably removed from the mixture by the carrier gas and is absorbed in water from the sample-acid mixture in a region spaced from the reactor. In this way, the carrier gas is freed of the hydrochloric acid gas and can be fed back to the sample-acid mixture in a circulatory system and reused.

Advantageously, the sample-acid mixture has a temperature of approximately 3° to 30° C., especially 10° to 20° C. Through this temperature it is assured, that the partial pressure of the VOC is kept low and the VOC remains largely retained in the liquid state in the sample.

In a further development, the water for the absorption of the hydrochloric acid gas is supplied to an analytical apparatus in a washing, or rinsing, process. Since it is usual to insert between one or more analytical processes following one after the other, in each case, a washing, or rinsing, step, the water contained in the washing, or rinsing, liquid and remaining in the analytical apparatus is utilized for reaction with the hydrochloric acid gas entrained in the carrier gas. An extra step for the introduction of the water can, thus, be omitted, so that the analytical apparatus is available very rapidly back for a new analytical step.

At the same time, the water supplied in the washing, or rinsing, procedure is utilized for removal from the analytical apparatus of the absorbate arising in the absorption the hydrochloric acid gas by the water. This absorbate deposits on the walls of the analytical apparatus and can be removed from the analytical apparatus easily in the washing, or rinsing, procedure.

In a further development, the method for removing chloride is performed as a batch process. The batch process, which is also known as a charge process, is a discontinuous process, in which a certain amount of the sample-acid mixture is subjected within a separate time interval to an ordered sequence of process activities.

Advantageously, the sample is a COD-sample or a TOC-sample. In the case of such samples, it is sufficient, when the mixture of the COD-sample or the TOC-sample with the acids has a volume of 0.5 to 50 ml, especially 2 to 10 ml. Already such small amounts are sufficient, in order to perform an exact analysis of the sample for a content of organic materials.

In an embodiment, the carrier gas is introduced finely distributed into the sample-acid mixture and has a volume flow of 20 to 2000 ml/min, especially 100 to 500 ml/min. With the very fine distribution and the high volume flow of the carrier gas assures that all of the entire hydrochloric acid gas contained in the sample-acid mixture is removed from the mixture, in order for the analysis to be performed to have a sample really free of chloride ions.

In a further development, the sample and/or the acids are cooled before introduction into the analytical apparatus. The cooling prevents the heat of dilution, which arises in the mixing of the liquid sample to be examined and the acids, from converting the predominant amount of the VOC into the gaseous phase. The VOC remains, thus, for the largest part, in liquid form in the sample.

Alternatively, the VOC-containing sample and the acids are mixed before introduction into the analytical apparatus, with the heat occurring in the mixing being removed. The evolved heat is given off to the environment after the mixing easily through a hose apparatus, which brings the mixture to the reactor. In this way, a cooling effect is obtained, so that the VOC largely remains in the sample.

In another variant, the analytical apparatus is cooled, in which the sample-acid mixture is contained. Also thereby, the effect is achieved, that the VOC for the predominant part contained in the sample remains in liquid form and does not escape therefrom in gaseous form.

Advantageously, the sample-acid mixture has an acid concentration of at least 50%. this concentration assures that the vapor pressure of the hydrochloric acid gas is sufficiently large, in order to be effectively purged.

Another further development of the invention relates to an analytical apparatus for performing the described method. In order to assure that chloride ions are safely removed from the samples containing volatile organic carbon, a gas inlet for a carrier gas is connected with a purging apparatus accommodating a sample-acid mixture. The purging apparatus is closed off from the atmosphere and leads to a separation chamber, on which adjoins an absorption chamber for separating hydrogen chloride gas from the carrier gas. The absorption chamber has a gas outlet for the carrier gas. This arrangement has the advantage, that the carrier gas moves in a circulatory system, in which it removes the hydrochloric acid gas from the sample-acid mixture in one portion and at another position of the analytical apparatus releases it and then is fed, as carrier gas freed of the hydrochloric acid gas, back to the sample-acid mixture.

Advantageously, the absorption chamber includes a zone wetted with water, wherein the water forms with the hydrochloric acid gas an absorbate. The analytical apparatus, thus, includes a separate region, in which the carrier gas is separated from the hydrochloric acid gas. The separated region is arranged in the circulatory system of the carrier gas behind the region containing the sample-acid mixture.

In a variant, the separation chamber is arranged horizontally between the approximately vertical purging apparatus and the likewise approximately vertical absorption chamber. In this way, a wetting of the walls of the absorption chamber is assured in the washing, or rinsing, procedure, since the washing, or rinsing, liquid in the filling of the purging apparatus overflows into the separation chamber. From the separation chamber, the washing, or rinsing, liquid drops onto the walls of the absorption chamber and forms, thus, on these the wetted zones.

In an embodiment, circulation of the carrier gas is accomplished by a pump system closed to the atmosphere connected suction-side with the gas removal outlet for the carrier gas and pressure-side with the gas inlet for the carrier gas. By means of the pump system, the carrier gas is kept continually moving during the analytical procedure, in order safely to provide, that the chloride ions are purged from the sample in the form of hydrochloric acid gas.

In a further development, an inlet for the sample and/or the acid is connected with the purging apparatus. The sample and the acid are charged into the purging apparatus before the analysis. In a compact and robust variant, the analytical system has only one inlet both for the liquid sample to be examined as well as also for the acid. In order safely to provide, that the heat of dilution, which arises in the mixing of sample and acid, developes first in the purging apparatus, it is of advantage, that the sample and the acid have separate inlets into the purging apparatus, since the purging apparatus is easy to cool for removing the heat of dilution.

Advantageously, is a supply system is linked to the first inlet for the sample and/or to the second inlet for the acid. In such case, a first supply system is available for delivery of the sample and a second supply system is available for delivery of the acid. These supply systems enable metering of the amounts of sample and acid introduced into the purging apparatus.

In an embodiment, there is arranged below the purging apparatus a liquid discharge, which is closable with a valve. Through the opened valve, the sample-acid mixture is removed from the purging apparatus, when the analytical procedure is ended. Also after termination of a washing, or rinsing, procedure, in the case of which preferably sample liquid is used as washing, or rinsing, agent, this washing, or rinsing, agent can be removed from the purging system. In the case of closed valve, a new sample-acid mixture is filled into the purging apparatus and provided for analysis.

In a further development the gas inlet for the carrier gas is arranged above the liquid outlet on the purging apparatus. In the case of closed valve of the liquid outlet and sample-acid mixture charged into the purging system, this constructively simple apparatus provides a circulatory system for the carrier gas.

Advantageously, below the wetted zone of the absorption chamber and the gas discharge for the carrier gas, there is provided a drain opening for removal of a rinsing liquid and/or for the absorbate of water and hydrochloric acid gas forming on the wetted zone. This drain opening can be embodied as a tube and forms a volumetric safety reserve for the pulsating volumetric head of the carrier gas brought about by the pump system. The head can expand or contract into this region. Thus, the carrier gas located in the circulatory system represents in first approximation a closed system, which can, indeed, exchange energy with the environment, while an exchange of material is largely suppressed.

In an embodiment, the purging apparatus is arranged between 1) a light source for irradiating the sample-acid mixture present in the purging apparatus along a light path and 2) a light receiver for the registering the intensity of the light emitted from the light source after its passing through the measuring path. By means of this simple apparatus, the chemical oxygen demand of the liquid sample is ascertained photometrically. The measuring path extends, in such case, between light source and light receiver through a reaction mixture, in the case of which to the sample-acid mixture an oxidizing agent is added. The sample-acid mixture is thereby digested in the purging apparatus for the measuring. The reaction mixture absorbs the transmitted light as a function of the COD-content of the sample. The so weakened light is received by the light receiver

BRIEF DESCRIPTION OF THE DRAWING

The invention enables numerous forms of embodiment. One embodiment therefrom will now be explained in greater detail on the basis of the drawing, the sole FIGURE of which shows as follows:

FIG. 1 shows an analytical apparatus for removing chloride from a VOC-containing, liquid sample, Equal features are designated with equal reference characters.

DETAILED DISCUSSION IN CONJUNCTION WITH THE DRAWING

Shown schematically in FIG. 1 is an analytical apparatus for removing chloride from a VOC-containing, liquid sample, especially a wastewater sample. The analytical apparatus includes a purging apparatus 1 of glass. For supplying the sample liquid, there are provided, opening into the purging apparatus 1, a first inlet 2 and, for a difficultly volatile acid, for example, sulfuric acid $H_2SO_4$ or phosphoric acid $H_3PO_4$, a second inlet 3. On the opposite end of the purging apparatus 1 is a narrowing outlet 4, controlled by a valve 6, which, in the closed state, retains the sample-acid mixture 5 located in the purging apparatus 1. Between the purging apparatus 1 and the valve 6 there opens into the outlet 4 a laterally connected gas inlet 7 for the carrier gas, which is brought into the sample-acid mixture 5. Examples of carrier gas include air, nitrogen $N_2$ or argon Ar.

The sample-acid mixture 5 does not fill the purging apparatus 1, so that between the inlets 2, 3 and the surface of the sample-acid mixture 5 a space arises, which can be filled with the carrier gas. In this region is connected at an angle of approximately 90° a gas discharge 8, to which a separation chamber 9 adjoins. Perpendicularly to the separation chamber 9 is arranged an absorption chamber 10, which has wetted zones 11. The absorption chamber 10 extends, in such case, essentially parallel to the purging apparatus 1.

The absorption chamber 10 ends in an outlet opening 12. Arranged beneath the absorption chamber 10 containing the wetted zones 11 is a lateral gas discharge 13 for the carrier gas, to which a line 14 is connected, which leads to a pump system 16 and forwards the carrier gas via a second line 15 to the gas inlet 7 for the carrier gas.

For supplying the liquid sample and the acid, advantageously, sulfuric acid, there serves for each a supply- and metering system 17, 18, wherein the first supply- and metering system 17 is responsible for introduction of the liquid sample into the inlet 2 and the second supply- and metering system 18 for introduction of the sulfuric acid into the inlet 3. Utilized as supply- and metering systems 17, 18 are peristaltic pumps, which work according to the peristaltic principle. However, also a single peristaltic pump can be utilized for both liquid supply lines.

Process flow for the removal of chloride ions from VOC-containing, COD, liquid samples by means of the analytical apparatus illustrated in FIG. 1 is, for example, as follows:

In a first method step, the purging apparatus 1 is rinsed with the liquid, which flows via the inlet 2 into the purging vessel. In such case, so much liquid is allowed into the purging vessel 1, that it is completely filled with the liquid. Overflowing liquid reaches, in such case, via the gas outlet 8 into the horizontally arranged separation chamber 9, from where it drops into the absorption chamber 10. In such case, there remain especially parts of the rinsing liquid in the absorption chamber 10 to form the wetted zone 11. Excess liquid is removed via the drain opening 12 from the analytical apparatus. Also removed from the purging apparatus 1 is the rinsing liquid. This is accomplished by opening the valve 6.

In a second step, valve 6 is closed and first a liquid sample is charged via the inlet 2 by means of the metering- and supply system 17 into the purging apparatus 1. To the liquid sample is then added into the purging apparatus 1 via the inlet 3 the sulfuric acid, which is metered by the second metering- and supply system 18, so that a sample-acid mixture 5 with a volume between 0.5 to 50 ml, preferably between 2 to 10 ml results. The sample-sulfuric acid-mixture 5 has, in such case, a sulfuric acid concentration of at least 50%. The sulfuric acid reacts with the chloride ions contained in the sample to hydrochloric acid gas, which is contained in dissolved form in the sample-acid mixture 5.

The purging apparatus 1 is cooled by means of a cooling system (not shown), so that the sample-acid mixture 5 has a temperature of 3° C. Through the cooling, the heat of dilution, which arises from the mixing of the liquid sample with the sulfuric acid, is removed. Thus, it is assured, that the VOC contained in the liquid sample for the most part remains.

Via the gas supply line 15, a carrier gas, preferably air, is introduced for purging the hydrochloric acid gas from the sample-acid mixture 5. The flow of the carrier gas is set at 20 to 2000 ml/min, preferably at 100 to 500 ml/min. The gas introduction occurs through fritted glass or a nozzle, so that the gas introduction is distributed finely over a large volume region of the sample-acid mixture 5 contained in the purging apparatus 1. The carrier gas leaves the purging apparatus 1 together with the hydrochloric acid gas taken from the sample-acid mixture 5 and passes through the gas discharge 8 into the separation chamber 9. In the absorption chamber 10, the hydrochloric acid gas reacts with the water, which was left clinging to the walls following the washing, or rinsing, process to form the wetted zone 11. Thus, the water absorbs the hydrochloric acid gas. The carrier gas freed of the hydrochloric acid gas is sucked by the pump 16 into the gas outlet 13 and the line 14 and fed via the line 15 and the gas inlet 7 back into the sample-acid mixture 5, whereby the procedure can begin anew.

After the hydrochloric acid gas is removed from the sample-acid mixture 5, there is supplied via a third inlet (not shown) an oxidizing agent, for example, a potassium dichromate solution. The reaction mixture so formed with the sample-acid mixture 5 is heated at atmospheric pressure and boiled under reflux conditions based on a cooling apparatus. Then, by means of a photometer (not shown) formed by a light source and a light receiver, the content of potassium dichromate remaining in the reaction mixture is ascertained.

From the light receiver detected intensity of the radiation of the light source transmitted through the reaction mixture, according to a method known per se, the absorption, or extinction, of the reaction mixture is ascertain and therefrom, on the basis of the known, originally present potassium dichromate concentration, the consumption of chromium (VI) is ascertained. This consumption is converted into oxygen equivalents, i.e. into a COD value.

The described analytical apparatus is suitable not only for determining COD value. The construction of the analytical apparatus permits simultaneously a reliable forming of wetted zones in the absorption chamber 11 during the washing, or rinsing, procedure for the removal of chloride from samples containing volatile organic carbon.

The invention claimed is:

1. Analytical apparatus for performing a method comprising the steps of:
   mixing a chloride containing sample with a low-volatile acid, wherein hydrochloric acid gas arises, which is present in dissolved form in the sample-acid mixture; purging the hydrochloric acid gas by a carrier gas from the sample-acid mixture; removing the hydrochloric acid gas from the carrier gas following said purging; feeding the carrier gas back to the sample-acid mixture, wherein the sample-acid mixture has a temperature of approximately 3° C. to 30° C.; and following said purging from the sample-acid mixture, the hydrochloric acid gas is removed from the carrier gas by absorption with water; the apparatus comprising:
a purging apparatus accommodating said sample-acid mixture;
a gas inlet for a carrier gas connected with said purging apparatus;
a separation chamber; and
an absorption chamber, wherein:
said purging apparatus is closed to the atmosphere and leads to said separation chamber adjoined by said absorption chamber for the separating of a hydrogen chloride gas from the carrier gas; and
an outlet of said absorption chamber is connected with a gas discharge for the carrier gas;
said absorption chamber has a zone wetted with water; and
the water reacts with the hydrochloric acid gas to form an absorbate.

2. The analytical apparatus as claimed in claim 1, wherein:
said separation chamber is arranged horizontally between said purging apparatus, which is approximately perpendicular, and said absorption chamber, which is likewise approximately perpendicular.

3. The analytical apparatus as claimed in claim 1, further comprising:
a pump system, wherein:
for circulation of the carrier gas, said pump system closed to the atmosphere is connected suction-side with said gas discharge for the carrier gas and pressure-side with said gas inlet for the carrier gas.

4. The analytical apparatus as claimed in claim 1, wherein:
an inlet for the sample and the acid is connected with said purging apparatus.

5. The analytical apparatus as claimed in claim 1, wherein:
a first inlet for the sample and a second inlet for the acid are connected with said purging apparatus.

6. The analytical apparatus as claimed in claim 5, further comprising:
a supply system connected to said first inlet for the sample.

7. The analytical apparatus as claimed in claim 1, wherein:
below said purging apparatus, a liquid outlet is arranged, which is closable with a valve.

8. The analytical apparatus as claimed in claim 7, wherein:
said gas inlet for the carrier gas is arranged on said purging apparatus above said liquid outlet.

9. The analytical apparatus as claimed in claim 1, wherein:
below the wetted zone of said absorption chamber and said gas discharge for the carrier gas, a drain opening is provided for removing a washing, or rinsing, liquid or the absorbate forming on the wetted zone from water and hydrochloric acid gas.

10. The analytical apparatus as claimed in claim 1, wherein:
said purging apparatus is arranged between a light source for irradiating the sample-acid mixture present in said purging apparatus along a measuring path, and a light receiver for registering intensity of light emitted from the light source after passing through the measuring path.

11. The analytical apparatus as claimed in claim 6, wherein:
said supply system is connected to said second inlet for the acid.

12. Analytical apparatus comprising:
a purging apparatus accommodating a sample-acid mixture;
a gas inlet for a carrier gas connected with said purging apparatus;
a separation chamber; and
an absorption chamber, wherein:
said purging apparatus is closed to the atmosphere and leads to said separation chamber adjoined by said absorption chamber for the separating of a hydrogen chloride gas from the carrier gas; and
an outlet of said absorption chamber is connected with a gas discharge for the carrier gas; and
said purging apparatus is arranged between a light source for irradiating the sample-acid mixture present in said purging apparatus along a measuring path, and a light receiver for registering intensity of light emitted from the light source after passing through the measuring path.

13. The analytical apparatus as claimed in claim 12, further comprising:
a first inlet for an oxidizing agent is connected with said purging apparatus.

14. The analytical apparatus as claimed in claim 13, wherein:
a second inlet for the sample and a third inlet for the acid are connected with said purging apparatus.

15. The analytical apparatus as claimed in claim 12, further comprising:
a cooling apparatus for cooling the purging apparatus.

16. The analytical apparatus as claimed in claim 13, wherein:
said oxidizing agent is potassium dichromate and said analytical apparatus is adapted to determine from the light intensity detected by the light receiver a COD value.

17. The analytical apparatus as claimed in claim 1, further comprising a cooling system which is designed to cool said purging apparatus.

* * * * *